(12) United States Patent
Froelich

(10) Patent No.: US 7,350,250 B2
(45) Date of Patent: Apr. 1, 2008

(54) HEAD POSITIONING DEVICE

(76) Inventor: Michael Froelich, 1659 Oak Park La., Helena, AL (US) 35080

( * ) Notice: Subject to any disclaimer, the term of this patent is extended or adjusted under 35 U.S.C. 154(b) by 74 days.

(21) Appl. No.: 11/033,052

(22) Filed: Jan. 10, 2005

(65) Prior Publication Data

US 2005/0160532 A1  Jul. 28, 2005

(51) Int. Cl.
*A47G 9/00* (2006.01)
*A61G 13/12* (2006.01)

(52) U.S. Cl. .............................. 5/637; 5/640; 128/869
(58) Field of Classification Search ................ 5/622, 5/637, 636, 640; 128/869, 870
See application file for complete search history.

(56) References Cited

U.S. PATENT DOCUMENTS

| | | | |
|---|---|---|---|
| 3,188,079 A | 6/1965 | Boetcker et al. | |
| 3,572,835 A | 3/1971 | Kees, Jr. et al. | |
| 3,957,262 A | 5/1976 | McReynolds | |
| 4,259,757 A | 4/1981 | Watson | |
| 4,545,572 A | 10/1985 | Day | |
| 4,918,774 A | 4/1990 | Popitz | |
| 4,979,519 A | 12/1990 | Chavarria et al. | |
| 5,048,136 A | 9/1991 | Popitz | |
| 5,081,665 A | 1/1992 | Kostich | |
| 5,207,716 A * | 5/1993 | McReynolds et al. | 5/637 |
| 5,682,632 A | 11/1997 | Cotroneo | |
| 5,916,189 A | 6/1999 | Sullenperger et al. | |
| 6,446,288 B1 | 9/2002 | Pi | |
| 6,594,839 B1 | 7/2003 | Papay | |
| 2003/0070684 A1 | 4/2003 | Saied | |

OTHER PUBLICATIONS

Sawin, Paul D.., Todd, Michael M., Traynelis, Vincent C., Farrell, Stella B., Nader Antoine, Sato, Yutaka, Clausen, John D., Goel, Vijay K., Cervical Spine Motion With Direct Laryngoscopy and Orotracheal Intubation, Spine (Journal), Jul. 1, 1996, pp. 26-36, vol. 85, No. 1, Lippincott-Raven Publishers, Iowa City, Iowa.

Orday, Nathaniel R., Seymour, Ronald J., Donelson, Ronald G., Hojnowski, Leonard S., Edwards, Thomas W., Cervical Flexion, Extension, Protrusion, and Retraction, Anesthesiology (Journal), 1999, pp. 240-247, vol. 24, Lippincott Williams & Wilkins, Inc.

Henrik W. Christensen, Niels Nilsson, Natural Variation of Cervical Range of Motion: A One-Way Repeated-Measures Design, Journal of Manipulative and Physiological Therapeutics, Jul./Aug. 1998, pp. 383-387, vol. 21, No. 6, JMPT, United States of America.

(Continued)

*Primary Examiner*—Alexander Grosz
(74) *Attorney, Agent, or Firm*—Alston & Bird LLP

(57) ABSTRACT

A head positioning device comprising: (A) a head support that is configured for supporting a patient's head; and (B) a sliding joint that is connected to allow the head support to be moved about a virtual axis of rotation while the head support is supporting the patient's head, wherein the virtual axis of rotation is spaced apart from the sliding joint. The head positioning device may include a head restraint for maintaining the patient's head in a substantially fixed relation to the head support as the head support is moved about the virtual axis of rotation. In one embodiment, the head restraint comprises a hook member that is configured for hookedly engaging a curved portion of the patient's face.

27 Claims, 7 Drawing Sheets

OTHER PUBLICATIONS

Aria V. Bulgheroni, Fabio Antonaci, Sara Ghirmai, Giorgio Sandrini, Giuseppe Nappi, Antonio Pedotti, A 3D Kinematic Method for Evaluating Voluntary Movements of The Cervical Spine in Humans, Journal of Functional Neurology, Jul./Sep. 1998, pp. 239-245, vol. XIII, No. 3, CIC Edizioni Internazionali, Italy.

* cited by examiner

HEAD POSITIONING DEVICE

BACKGROUND OF THE INVENTION

Endotracheal intubation and laryngoscopy are techniques that are often practiced by anesthesiologists in, for example, operating rooms, intensive care units, and emergency rooms. Most anesthesia textbooks recommend moving a patient's head into the "sniffing position" before intubating the patient. When a patient's head is in the sniffing position, typically: (1) the patient's head is elevated; (2) the patient's neck is extended; and (3) the patient's axis of vision is relatively well aligned with the axis of the patient's glottis. More specifically, the sniffing position is typically achieved when the oropharyngeal, laryngeal, and tracheal axes of the patient's head and neck are at least substantially aligned. Placing a patient's head into the sniffing position is desirable to give the practitioner intubating the patient as clear of a view as possible of the patient's glottis and vocal cords to successfully guide the intubation tube into the patient's trachea without injuring the patient.

Different techniques have been developed to assist practitioners in moving a patient's head into the sniffing position and maintaining it there. For example, most anesthesiologists use a standard blanket or pillow to maintain a patient's head in the sniffing position. However, standard pillows and blankets are typically ineffective at maintaining the patient's head in the sniffing position while the patient is being intubated.

As a result, many physicians manually extend the patient's head into the sniffing position and then manually maintain the patient's head in this position while intubating the patient. To do this, the physician may, for example, position their free hand under the back of the patient's neck and lift until the patient's head is extended. Alternatively, the physician may pull the patient's head back into the sniffing position by applying manual traction to the patient's hard palate. However, these maneuvers to improve head position can not be maintained through the actual intubation because the physician needs to use both hands to intubate the patient. In particular, the physician need to use one hand to manipulate the laryngoscope and the other to insert the endotracheal tube.

Another technique for positioning and maintaining a patient's head in a sniffing position involves positioning a laryngoscope within the patient's endotracheal airway and then lifting upwardly to pull on the patient's jaw and the basis of the patient's tongue to maintain the patient's head in extension. This technique requires the physician to apply a significant amount of force to the patient's jaw and tongue in order to maintain the patient's head in the sniffing position. This may cause damage to the patient's airway, lips, or teeth.

In light of the above, there is a need for an improved head positioning device that is capable of positioning the patient's head in a sniffing position efficiently without causing trauma or injury to the patient, and for maintaining the patient's head in the sniffing position while the patient is being intubated.

BRIEF SUMMARY OF THE INVENTION

A head positioning device according to one embodiment of the invention comprises: (1) a head support that is configured for supporting a patient's head; and (2) a sliding joint that is connected to allow the head support to be moved about a virtual axis of rotation while the head support is supporting the patient's head; and optionally (3) an elevating mechanism to lift the patient's head upward from a supine position. In this embodiment, the virtual axis of rotation is spaced apart from the sliding joint.

A head positioning device according to a further embodiment of the invention comprises: (1) a head support that is configured for supporting a patient's head, the head support being configured for engaging a rear portion of the patient's head; and (2) a head restraint disposed adjacent the head support, the head restraint comprising a hook member that is configured for: (A) hookedly engaging a curved portion of the patient's face; and (B) exerting a force adjacent the curved portion of the patient's face. In a particular embodiment, the force is sufficient to move the patient's forehead away from the patient's chest through an extension (retroflexion) motion about the patient's cervical spine.

A head positioning device according to yet another embodiment of the invention comprises: (1) a head support that is configured for supporting a patient's head, the head support being configured for engaging a rear portion of the patient's head; and (2) a head restraint disposed adjacent the head support, the head restraint being configured for: (A) engaging a portion of the patient's face; and (B) exerting a force adjacent the portion of the patient's face, the force being sufficient to move the patient's head into a sniffing position (e.g., neck extension and head elevation in a supine patient) while the head support is supporting the patient's head.

BRIEF DESCRIPTION OF THE DRAWINGS

Figure 1:
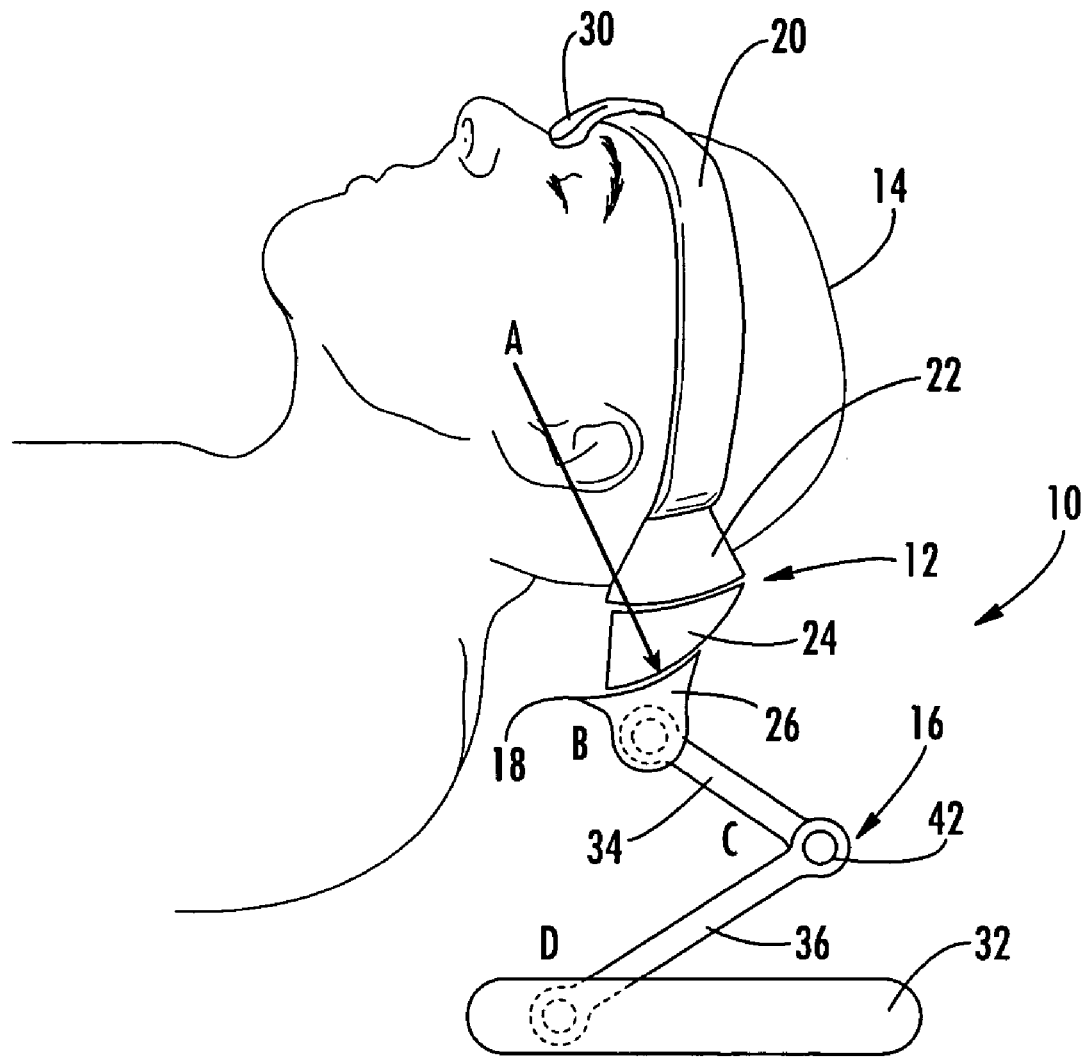

Having thus described various embodiments of the invention in general terms, reference will now be made to the accompanying drawings, which are not necessarily drawn to scale, and wherein:

FIG. 1 is a side view of a head positioning device according to a particular embodiment of the invention.

Figure 2:
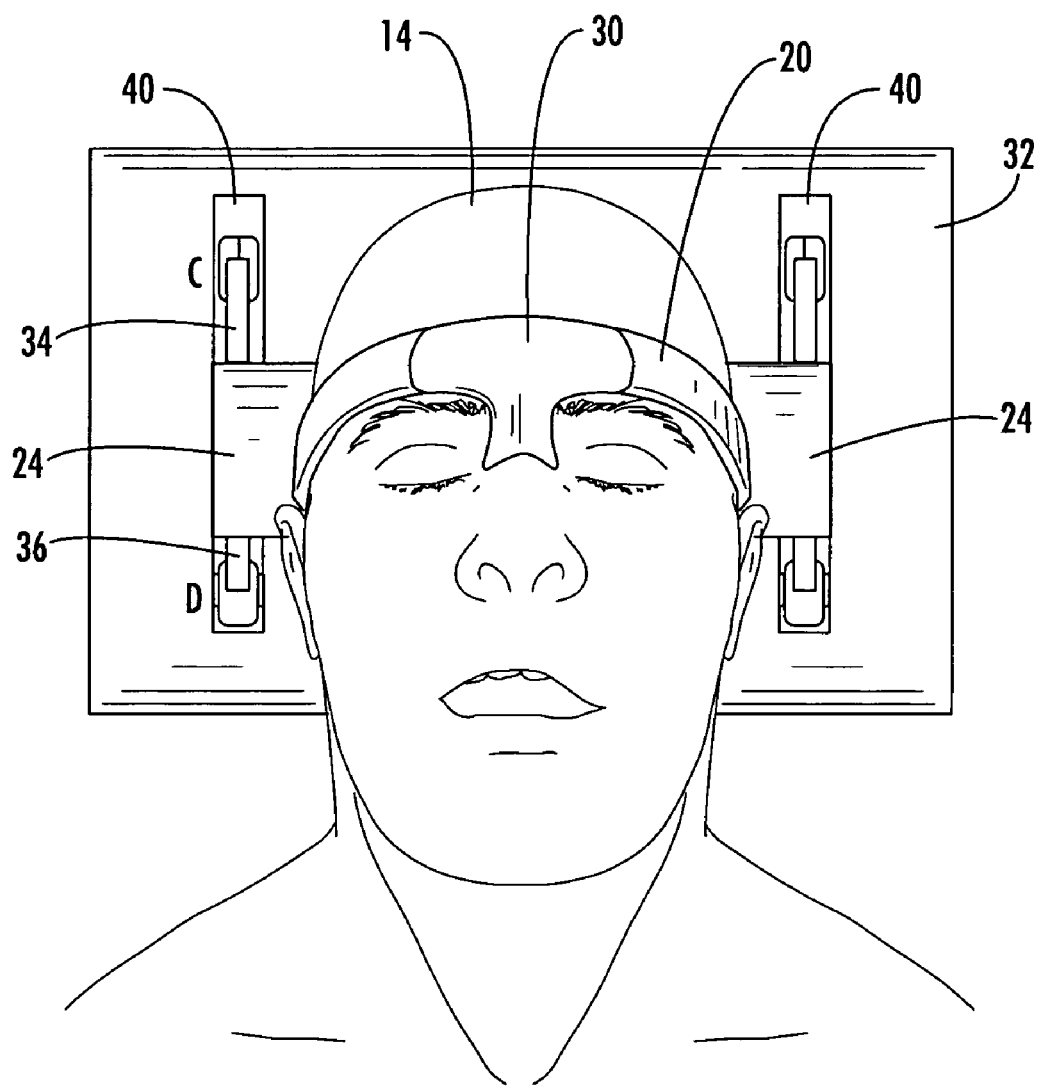

FIG. 2 is top view of a head positioning device according to a particular embodiment of the invention. This figure shows a head restraint including a hook member configured for hookedly engaging a curved portion of a patient's head.

Figure 3:
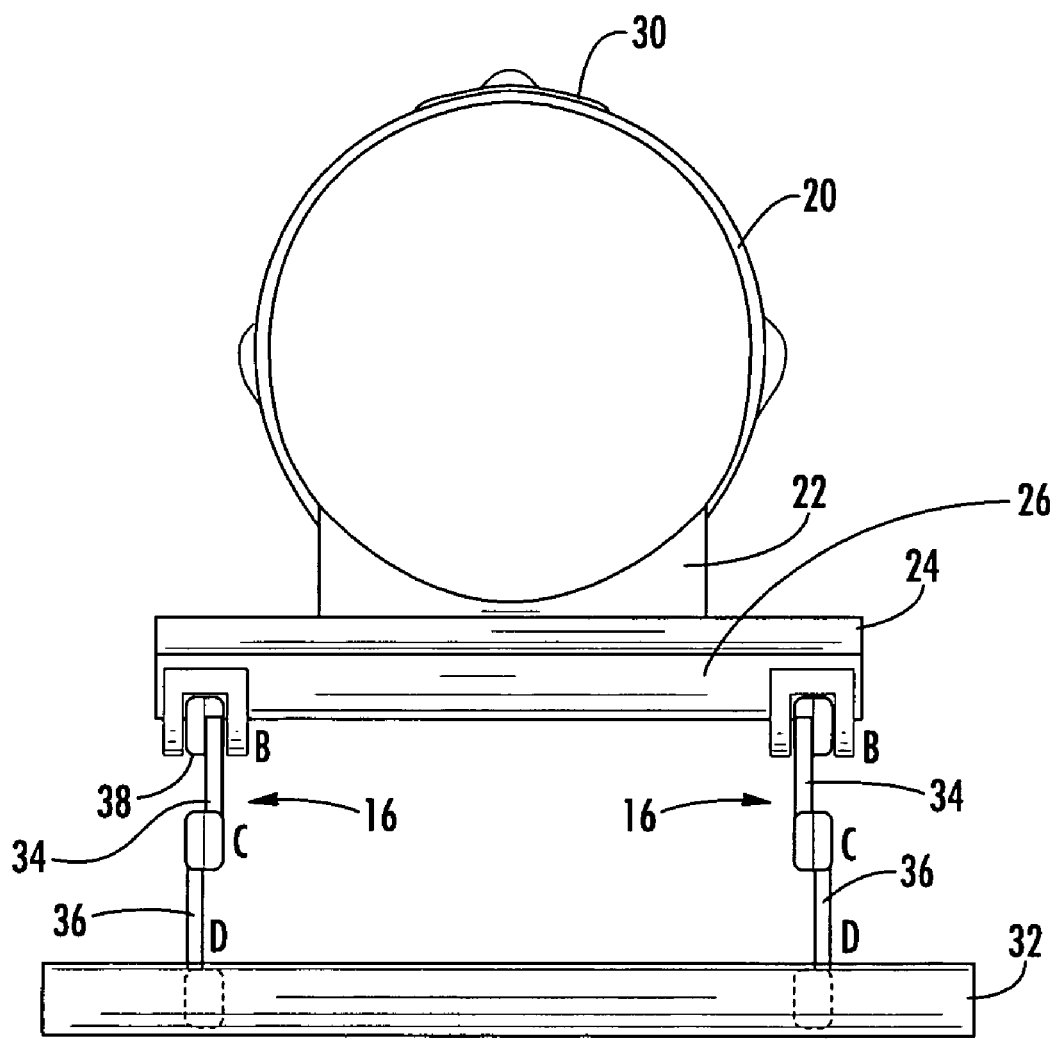

FIG. 3 is a rear view of a head positioning device according to one embodiment of the invention. This figure shows a pair of elevating mechanisms positioned on opposite ends of a head support.

Figure 4:
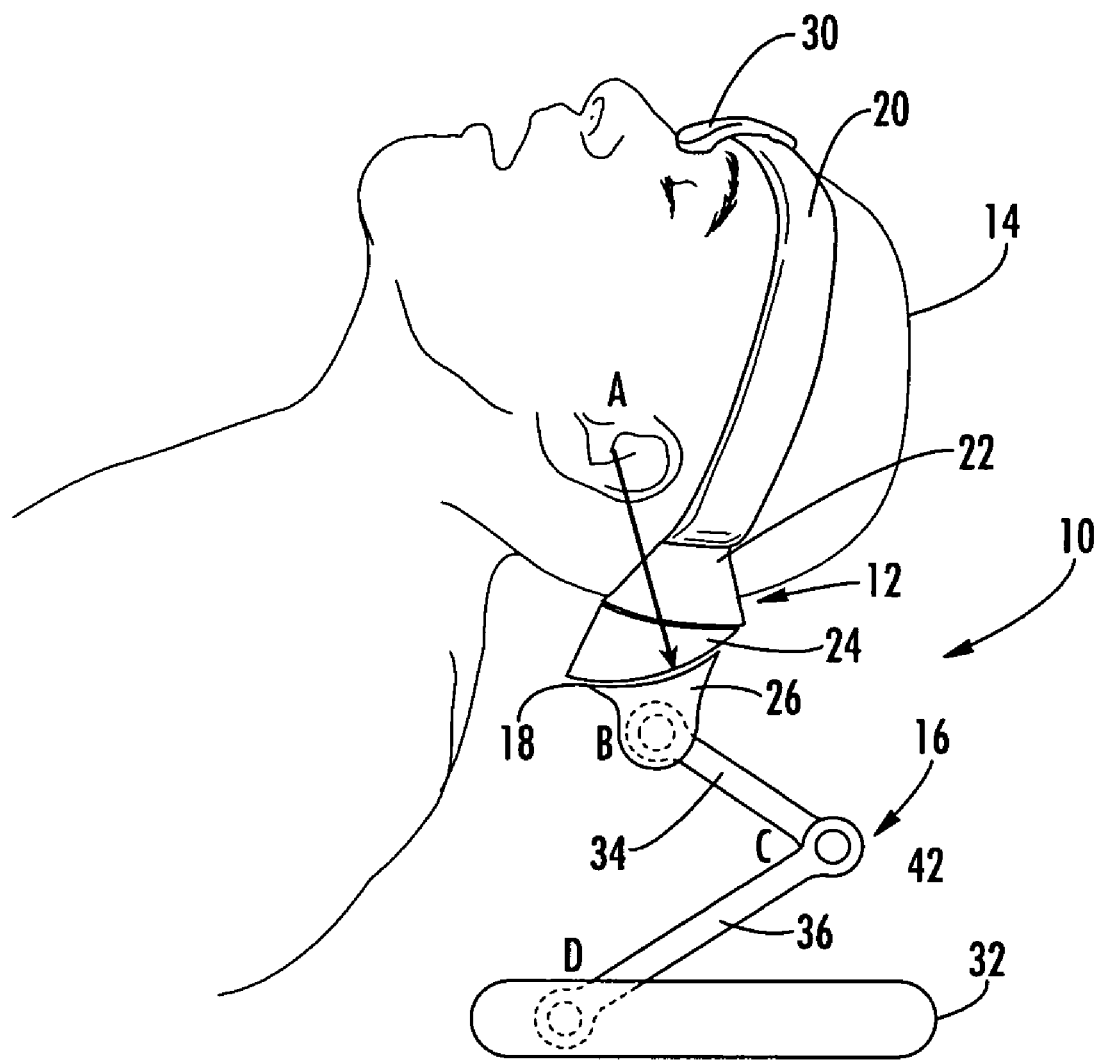

FIG. 4 is a side view of a head positioning device according to a particular embodiment of the invention. This figure shows how one embodiment of the head positioning device may be use to maintain a patient's head in a "sniffing position".

Figure 5:
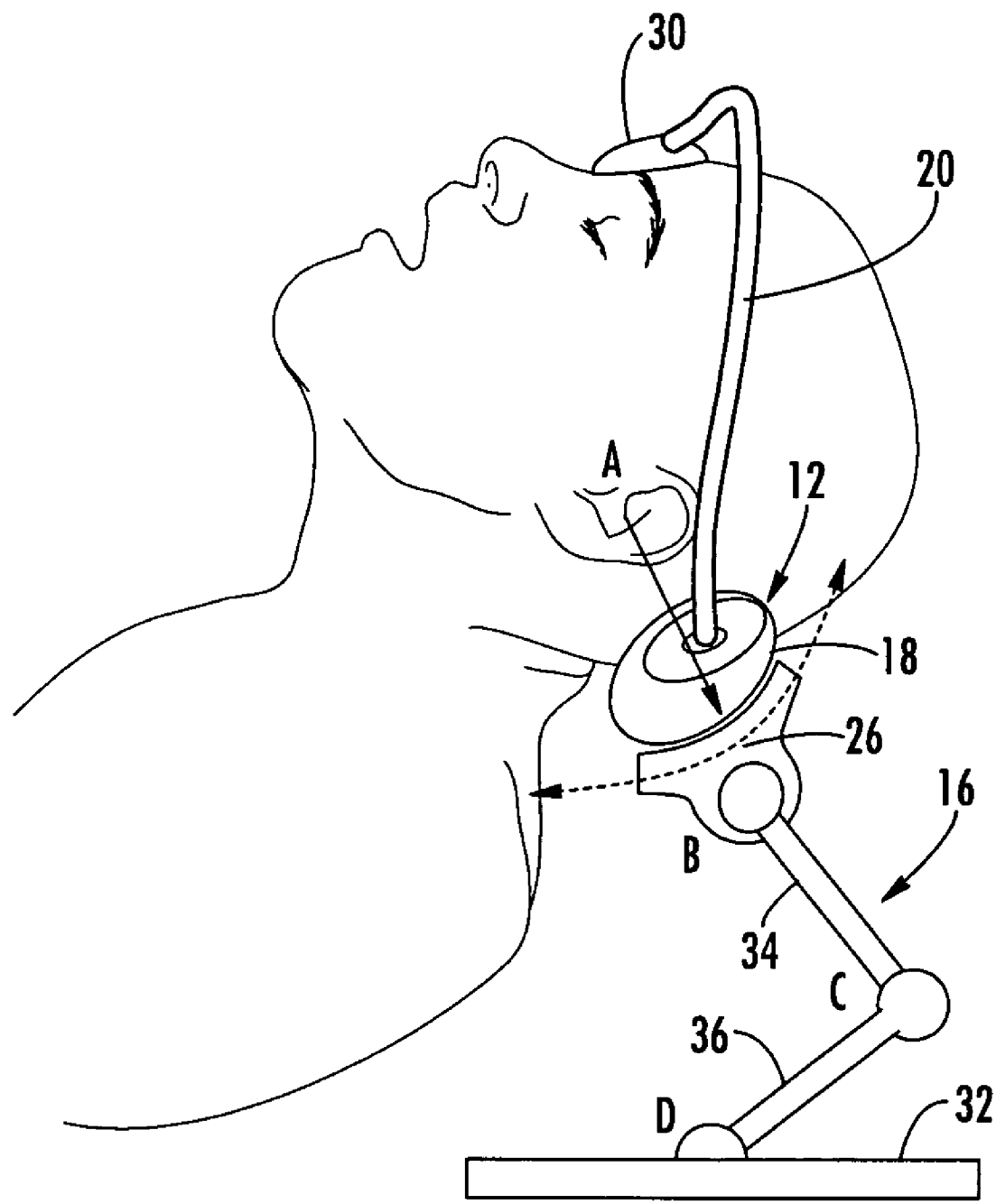

FIG. 5 is a side view of a head positioning device according to another embodiment of the invention.

Figure 6:
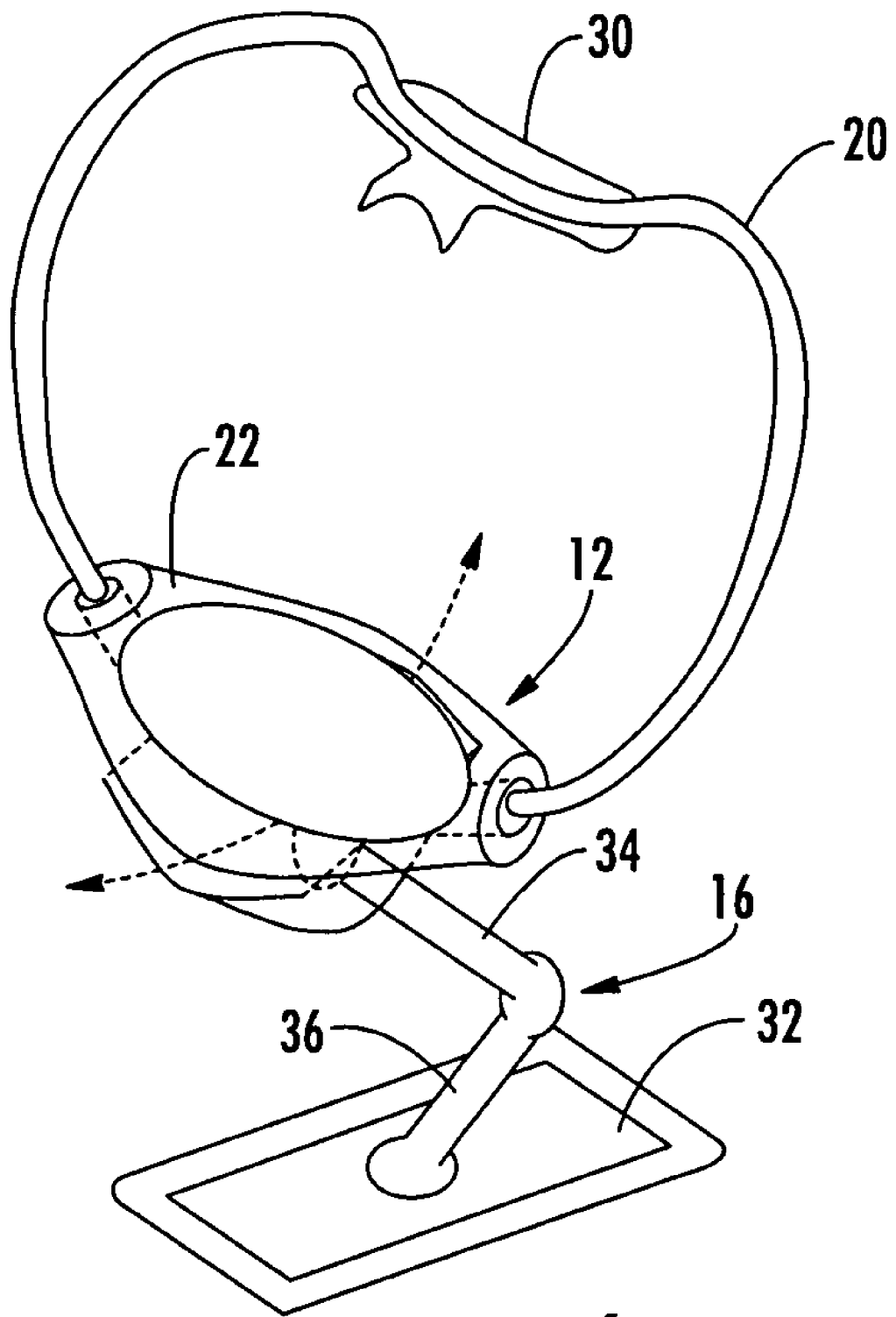

FIG. 6 is a perspective view of the head positioning device according to a particular embodiment of the invention.

Figure 7:
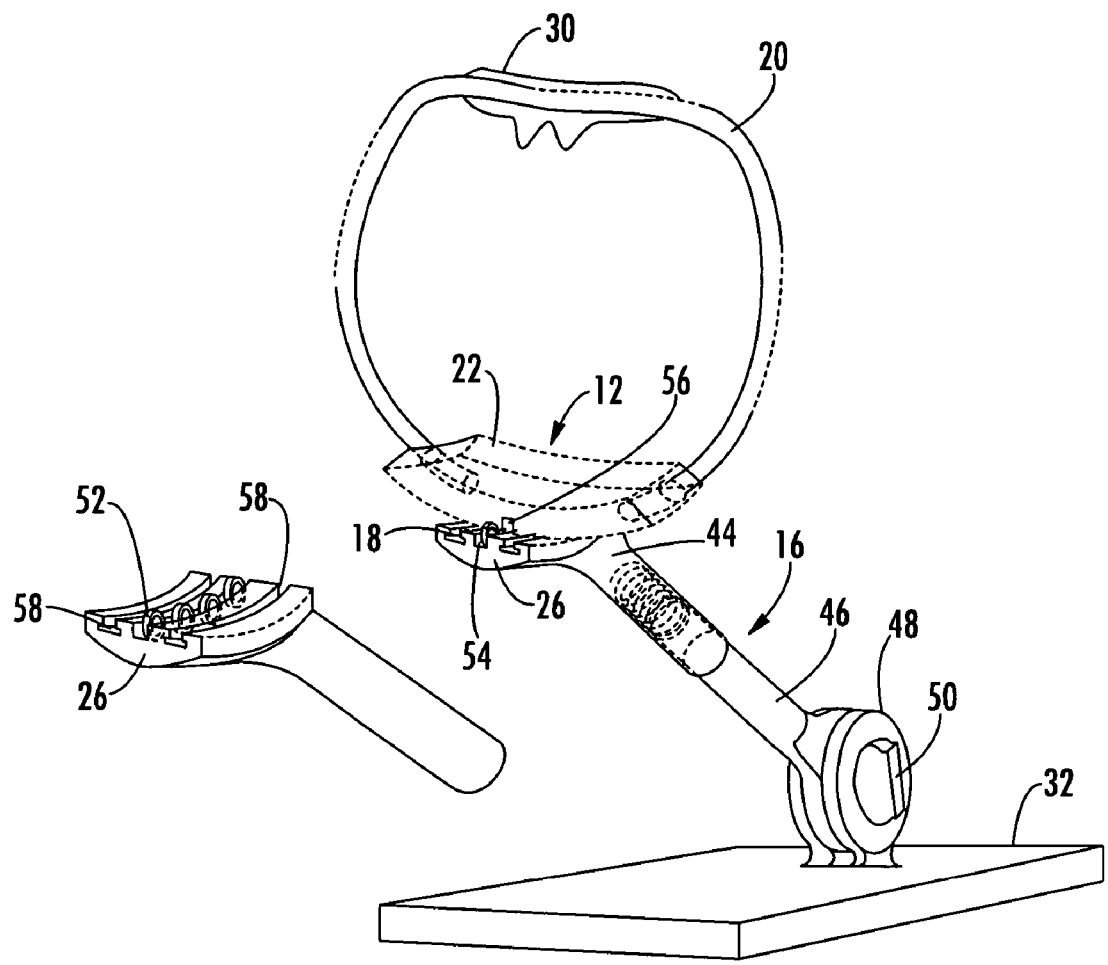

FIG. 7 is a perspective view of a head positioning device according to another embodiment of the invention. This figure further includes an enlarged view of the first head positioning device's first telescoping member and sliding joint base member.

DETAILED DESCRIPTION OF THE INVENTION

The present invention now will be described more fully with reference to the accompanying drawings, in which some, but not all embodiments of the invention are shown.

As will be understood by one skilled in the relevant field, this invention may be embodied in many different forms and should not be construed as limited to the embodiments set forth herein. Rather, these embodiments are provided so that this disclosure will satisfy applicable legal requirements. Like numbers refer to like elements throughout.

I. Overview of Head Positioning Device

FIG. 1 depicts a head positioning device 10 according to one embodiment of the present invention. As may be understood from this figure, in this embodiment, the head positioning device 10 comprises a head support 12 for supporting a patient's head 14, and an elevating mechanism 16 for positioning the head support in a predetermined position. In this embodiment, the head support 12 and the elevating mechanism 16 are connected by a sliding joint 18. In a particular embodiment of the invention, the sliding joint 18 defines a virtual axis of rotation A. In this embodiment, a head restraint 20 is attached adjacent the head support 12 and is configured to secure the patient's head 14 adjacent the head support 12 as the patient's head is moved about the virtual axis of rotation A.

In a particular embodiment of the invention, the head positioning device 10 is configured to rotate the patient's head 14 about the virtual axis of rotation A between a non-extended position (See e.g., FIG. 1) and a "sniffing position" (See e.g., FIG. 4). In one embodiment, the head support 12 and elevating mechanism 16 cooperate to maintain the patient's head 14 in a sniffing position during medical procedures such as endrotracheal intubation, laryngoscopy, or tracheoscopy. Moreover, in various embodiments, the head positioning device 10 may be adapted to facilitate positioning the patient's head into one or more of a variety of other desirable positions while supporting the patient's head 14.

The structure of the head support 12, elevating mechanism 16, sliding joint 18, and head restraint 20 will now be described in greater detail.

Structure of the Head Support

In one embodiment of the invention, the head support 12 comprises a first support member 22 and a second support member 24. As shown in FIG. 3, in this embodiment, the first support member 22 is sufficiently wide to support a posterior portion of the patient's head 14. In a particular embodiment, the second support member 24 extends laterally slightly beyond the lateral ends of the first support member 22 and is connected adjacent (and preferably to) a sliding joint base member 26 to form a sliding joint 18.

In one embodiment, the first support member 22 defines a substantially concave profile that is adapted to conform to a posterior portion of the patient's head 14. This posterior portion may be, for example, proximate to the occipital portion of the patient's skull. It should be understood that the head support 12 may have various curvatures (or no curvature at all) in additional embodiments. For example, the first support member 22 could extend from the posterior portion of the patient's head and circumferentially about the patient's head to conform to at least a portion of the temporals of the patient's skull.

In a particular embodiment, the first 22 and/or second 24 support members are configured to support the patient's head 14 while not substantially deforming due to the weight of the patient's head. The first support member 22 may include padding along the contour of the first support member's concave surface to increase comfort. In various embodiments of the invention, the first support member 22 comprises a gel pad.

It should be understood that the first 22 and second 24 support members may be in any of a variety of different lengths and configurations that are, for example, suitable to support the patient's head 14 and to slideably connect to the sliding joint base member 26. For instance, the first 22 and second 24 support members could be parts of a single piece and/or could be the same length in various embodiments. For instance, in FIGS. 5 and 6, the head support 12 is a single member having a concave curvature that is adapted to conform to a posterior portion of the patient's head, and connects with the sliding joint base member 26 to form a sliding joint 18.

Structure of the Head Restraint

In one embodiment of the invention, a head restraint 20 is adapted to attach adjacent the head support 12 and to extend about a portion of the patient's head 14. In various embodiments, the head restraint 20 extends circumferentially about the patient's head 14 and forehead. In various embodiments, the head restraint 20 is substantially rigid. In other embodiments, the head restraint 20 may be somewhat flexible, which facilitates adjusting the head restraint to fit a particular patient's head 14. As depicted in FIG. 2, in one embodiment of the invention, the head restraint 20 is generally configured as an arcuate headband that is adapted to substantially encircle a patient's head 14.

FIG. 1 illustrates that, in various embodiments, at least one end of the head restraint 20 (and preferably both ends of the head restraint 20) attaches adjacent the first support member 22 to maintain the head restraint 20 in place adjacent the first support member 22. In a particular embodiment, the head restraint 20 is a rigid, substantially U-shaped bar that may be fixedly attached in place about a patent's head 14 to maintain the patient's head 14 in place adjacent the head restraint 20. In another embodiment, the head restraint is flexible and one end of the head restraint 20 includes a fastener (not illustrated), such as Velcro®, to secure and adjust the head restraint 20 about the patient's head.

It should be understood that the head restraint 20 could be made of various materials including, for example, a rigid polymeric material, such as polypropylene, that is capable of both securing the patient's head 14 adjacent the head support 12 and for providing some flexibility for allowing the size of the head restraint to be adjusted. A layer of foam (not illustrated) may be provided adjacent an inner surface of the head restraint 20 to provide, for example, padding and frictional resistance to prevent the head restraint from slipping out of position or off of the patient's head.

In a further embodiment of the invention, which is shown in FIGS. 5 and 6, the head restraint 20 comprises a wire that substantially encircles the patient's head 14. As illustrated in FIG. 6, in this particular embodiment, the head restraint 20 is preferably a substantially rigid wire that is fixed adjacent the head support 12 by inserting one or both ends of the rigid wire into channels defined by the head support 12.

In a particular embodiment of the invention, one or both ends of the head restraint 20 are adapted to selectively slide within the channels of the head support 12 to adjust the circumference of the head restraint, and to be locked in place when the desired circumference is reached.

As shown in FIGS. 6 and 7, the head restraint 20 may be a substantially U-shaped wire or bar (e.g., a metal wire or bar) that is adapted so that its ends may be received into ratcheted openings defined in the first support member 22 and so that the head restraint 20 may be slid into and out of the ratcheted openings to adjust the head restraint 20 about the patient's head 14, but also lock once a desired tightness and position is achieved.

In one embodiment of the invention, the head restraint 20 comprises a hook member 30 that is preferably configured to hookedly engage a curved portion of a patient's face. For example, FIG. 2 shows a hook member 30 engaging a patient's glabella, which, as will be understood by one skilled in the relevant field, is the portion of the patient's face located adjacent the root of the patient's nose. In one embodiment, the hook member 30 is configured to engage the patient's head 14 (in this case, the patient's face) to transfer rotational force to the patient's head 14 such that movement of the head support 12 about the sliding joint 18 also causes the patient's head 14 to rotate about the sliding joint's axis of rotation. Thus, the hook member 30 exerts a force on the patient's head that is sufficient to facilitate movement of the patient's forehead away from the patient's chin to a sniffing position, such as the sniffing position shown in FIG. 4. Similarly, in various embodiments, the hook member 30 cooperates with the head restraint 20 to maintain the patient's head 14 in the sniffing position.

In one embodiment of the invention, at least 40% of the force required to move the patient's head 14 from a non-extended position (See e.g., FIG. 1) to a sniffing position (See e.g., FIG. 4) and/or to maintain the patient's head in the sniffing position is provided by the hook member 30. In various embodiments, the head restraint 20 provides substantially the remaining amount of restraining force required to move the patient's head 14 from a non-extended position to a sniffing position and/or to maintain the patient's head in the sniffing position. Accordingly, in particular embodiments, the head restraint 20 and the hook member 30 cooperate to restrain the patient's head 14 adjacent the head support 12.

In various embodiments of the invention, when the patient's head 14 is sufficiently restrained by the head restraint 20 and the hook member 30, movement of the head support 12 about the sliding joint 18 causes the patient's head to follow a path of movement about the sliding joint's virtual axis of rotation A. In addition, in a particular embodiment, the head restraint 20 and hook member 30 cooperatively restrain the patient's head 14 in the sniffing position, or other similar position, such that the patient's head does not rotate out of dorsiflexion, and the patient's neck does not relax out of extension.

In one embodiment of the invention, the hook member 30 is adapted to be removeably attached to the head restraint 20. In addition, in various embodiments of the invention, the hook member 30 may be adapted to extend adjacent, and to engage, both a portion of the patient's forehead and the patient's glabella when the head restraint 20 is in use. However, it should be understood that, in other embodiments, the hook member 30 may extend along and/or engage other parts of the patient's head 14, such as the patient's eyebrows or cheek bones. Similarly, the head positioning device 10 may include a plurality of hook members 30 for engaging the patient's head 14. This may serve, for example, to distribute the force needed to pull back the patient's head 14 over a greater amount of surface area on the patient's head 14. For example, the head restraint 20 may comprise a pair of hook members 30, and may be configured so that each of the hook members 30 engages a respective eye socket of the patient's head 14.

In various embodiments, a particular hook member 30 may further comprise deformable foam padding, or similar padding material, along the portion of the hook member 30 that is positioned to contact the patient's head 14. This may help, for example, to prevent compression of the divisions of the supraorbital nerve to increase comfort for the patient. In various embodiments, the hook member 30, like the head restraint 20, is substantially rigid, and is made of a substantially rigid material, such as polypropylene.

In a particular embodiment of the invention shown in FIGS. 5 and 6, the hook member 30 is adapted to clip adjacent the head restraint 20. Also, in various embodiments, the hook member 30 may be replaceable. In certain embodiments, the head restraint 20 is adapted so that the head restraint can be selectively equipped with any one of a plurality different sizes of hook members 30.

In one embodiment, the hook members 30 are disposable. For instance, a deformable foam may line an interior portion of the hook member 30 such that the foam conforms to a portion of a particular patient's face, but does not recover back to its original form. This particular type of foam is suitable for use with a disposable version of the hook member 30.

Structure of the Elevating Mechanism

As may be understood from FIG. 4, in one embodiment, the head positioning device 10 includes an elevating mechanism 16 that extends between the head positioning device's sliding joint base member 26 and the head positioning device's base portion 32. In certain embodiments, the elevating mechanism 16 comprises first 34 and second 36 elevating members that collectively form a linkage. In the embodiment shown in FIG. 4, the first elevating member 34 is pivotable about pivots B and C, and the second elevating member 36 is pivotable about pivots C and D. In various embodiments, the first 34 and second 36 elevating members cooperate to elevate or lower the patient's head 14 to various positions.

As shown in FIGS. 1 and 3, in one embodiment of the invention, the head positioning device 10 includes a pair of elevating mechanisms 16 positioned proximate to opposed lateral ends of the second support member 24. In various embodiments, each lateral end of the sliding joint base member 26 preferably includes a slot 38 that is configured for receiving one end of a corresponding first elevating member 34. This facilitates the pivotable attachment of the first elevating members 34 adjacent the sliding joint base member 26.

Similarly, as shown in FIGS. 1 and 2, in various embodiments, the base portion 32 also preferably includes a pair of slots 40, each of which is configured for receiving one end of a corresponding second elevating member 36. This facilitates the pivotable attachment of the second elevating members 36 adjacent the base portion 32. The free ends of the corresponding first and second elevating members 34, 36 are then pivotably attached to each other as shown in FIGS. 1 and 3.

It should be understood that any configuration and number of elevating mechanisms 16 and/or slots 38 and 40 may be used in alternative embodiments to accomplish raising and lowering the sliding joint base member 26. Also, other types of appropriate raising/lowering mechanisms may be implemented for this purpose.

As will be understood by one skilled in the art in light of this disclosure, various appropriate mechanisms may be used for: (1) pivotably attaching the first elevating member 34 adjacent the sliding joint base member 26, (2) pivotably attaching the second elevating member 36 adjacent the base portion 32, and (3) pivotably attaching the first elevating member 34 to the second elevating member 36.

In one embodiment of the invention, one or more (and preferably all) of the pivots B, C, and D are configured to allow the user to selectively lock and unlock the pivots B, C, D, preferably via a single locking/unlocking activation device. This allows a user to easily move the patient's head into the desired position, and then lock the various linkages (e.g., the first and second elevating members 34, 36) in place to hold the patient's head in the desired position.

In various embodiments of the invention, one or more of the pivots B, C, and D is configured to permit selective rotation of the first 34 and second 36 elevating members about the pivots B, C, and D. In one embodiment, one or more of the pivots B, C, and D may include a locking mechanism (such as a thumb screw or ratcheting mechanism) that is adapted to facilitate locking the first 34 and second 36 elevating members in a desired elevated position.

A particular embodiment of the present invention depicted in FIGS. 5 and 6, includes a single elevating mechanism 16. The elevating mechanism 16 may be connected adjacent the sliding joint base member 26 via, for example, a lockable ball-in-socket connector at pivot B. In addition, the first 34 and second 36 elevating members may be configured to rotate about pivots C and/or D via a similar lockable ball-in-socket connector.

In a further embodiment of the present invention depicted in FIG. 7, the elevating mechanism 16 includes first 44 and second 46 telescoping members. The second telescoping member 46 may slide within the first telescoping member 44, or vice versa, to adjust the relative height of the head support 12 and sliding joint base member 26. The first 44 and second 46 telescoping members may include, for example, a ratchet or similar locking mechanism for locking the first and second telescoping members 44, 46 in fixed relation to one another at a predetermined height. In one embodiment of the invention, the elevating mechanism 16 includes a release handle 50 (that may be remote from the locking mechanism) that is adapted to selectively unlock the locking mechanism so that the first and second telescoping members 44, 46 may be realigned to make further height adjustments.

In various embodiments of the invention, a first end of the first telescoping member 44 is attached to the sliding joint base member 26 and a second end of the first telescoping member 44 is slideably attached adjacent a first end of the second telescoping member 46. In particular embodiments, a second end of the second telescoping member 46 is pivotally attached adjacent the base portion 32 via a ratchet mechanism 48. This ratchet mechanism 48 may be configured, for example, for selectively allowing the second telescoping member 46 to rotate about the ratchet mechanism 48 in a first direction (e.g., away from the base portion 32), but not in a second direction (e.g., toward the base member). Thus, in various embodiments, a user may pivot the second telescoping member 46 about the ratchet mechanism 48 to adjust the angle of the elevating mechanism 16 until the patient's head is in a desired position. Once the patient's head is in this position, the ratchet mechanism 48 maintains the elevating mechanism at a predetermined angle (e.g., that corresponds to the desired position referenced above).

In one embodiment of the invention, a release mechanism may be used to release the ratchet mechanism 48 and thus allow the second telescoping member 46 to move in the second direction referenced above. This may, for example, allow the telescoping member 46 to move toward the base portion 32. In one embodiment of the invention, this same release mechanism may also be used to selectively unlock the locking mechanism referenced above to release the first 44 and second 46 telescoping members.

Structure of the Sliding Joint

In one embodiment of the invention, the sliding joint 18 is generally defined between the head support 12 and the elevating mechanism 16. In the particular embodiment shown in FIGS. 1-4, the second support member 24 and the sliding joint base member 26 cooperate to define the sliding joint 18. In one embodiment of the invention, the second support member 24 includes a convex surface that substantially mates within a concave surface of the sliding joint base member 26. In this configuration, the convex surface of the second support member 24 is adapted to slide adjacent the concave surface of the sliding joint base member 26. In one embodiment, the second support member 24 is adapted to continue to substantially mate with the concave surface of the sliding joint base member 26 while the second support member 24 slides adjacent the concave surface of the sliding joint base member 26.

In one embodiment, the second support member 24 is adapted to slide along an arc defined by the sliding joint's axis of rotation A, between: (1) a first position along the arc; and (2) a second position along the arc, the second position being spaced apart from the first position by at least 30 degrees. It should be understood that the head support 12 and sliding joint base member 26 may be in various configurations and curvatures to obtain any appropriate extent of rotation.

In a particular embodiment of the present invention, the head support 12 and sliding joint base member 26 are manufactured from materials that promote sliding and that minimize friction along the sliding joint 18. For example, the head support 12 and sliding joint base member 26 may comprise, for example: (1) a polymeric material, such as polyamide; (2) a metal and/or (3) an appropriate ceramic material. Further, various lubricants or bearings may also be employed in additional embodiments of the present invention to facilitate sliding within the sliding joint 18.

In various embodiments of the invention, the sliding joint 18 includes a braking or ratcheting mechanism to selectively prevent the various components of the sliding joint 18 from sliding relative to each other. This helps to maintain the patient's head in the sniffing position. For example, a ratchet and pawl mechanism may be used to allow the head support 12 to slide in a particular direction (e.g., in a direction that would move the patient's head 14 toward a dorsiflexed position) relative to the sliding joint base member 26, but to selectively restrict the head support 12 from sliding in the opposite direction relative to the sliding joint base member 26. A release handle or similar mechanism may be utilized to release the ratcheting mechanism to allow the patient's head 14 to move from the dorsiflexed position (e.g., into a non-extended position).

FIG. 7 illustrates an embodiment of the invention in which the sliding joint 18 includes a plurality of wheels 52 that are adapted to facilitate the movement of the head support 12 relative to the sliding joint base member 26. In particular, in this embodiment, one or more wheels 52 are rotatably mounted within a first sliding joint base member slot 54 that is defined by the sliding joint base member 26. In a particular embodiment, the head support 12 defines a head support slot 56 that is adapted to receive a portion of one or more of the wheels 52 that extends out of the first sliding joint base member slot 54. In a particular embodiment of the invention, the head support 12 and sliding joint base member 26 are configured so that the wheels 52 facilitate the ability of the head support 12 to slide relative to the sliding joint base member 26. In particular, in one embodiment, at least a portion of the head support 12 is supported by at least one of the wheels 52, and the wheels 52 rotate to facilitate the sliding movement of the head support 12 relative to the sliding joint base member 26.

Again referring to the embodiment shown in FIG. 7, in this embodiment, a pair of substantially T-shaped ridges (not shown) extends from the head support 12 to engage respective substantially T-shaped channels 58 that are defined by the sliding joint base member 26. This allows the head support 12 to slide relative to the sliding joint base member 26 without becoming detached from the sliding joint base member 26.

As described above, a braking or similar locking mechanism may be employed which allows the head support 12 to slide relative to the wheels 52 but that may be used to selectively lock the head support 12 in a predetermined position relative to the bearing member 26. In one embodiment, the braking mechanism may be unlocked with the release handle 50 or an additional releasing mechanism located adjacent the head positioning device 10.

As depicted by the arrow extending from the virtual axis of rotation A in FIG. 1, in one embodiment, the head positioning device 10 is configured so that the patient's head 14 rotates about the virtual axis of rotation as the head support 12 pivots about the sliding joint base member 26. Specifically, in this embodiment, the arcuate path of the sliding joint 18 extends along the circumference of a circle having its center defined along the virtual axis of rotation A. In a preferred embodiment, the virtual axis of rotation A extends through (or proximate) the mastoid region of the patient's head 14. Rotating the patient's head 14 about a virtual axis of rotation A defined through the mastoid region may serve to allow the patient's head to rotate about its natural axis of rotation, which may, for example, reduce the amount of force required to position the patient's head in dorsiflexion and the patient's neck in extension. Therefore, rotating the patient's head 14 about the virtual axis of rotation A that extends proximate to the mastoid region may serve to reduce the strain and potential injury on the patient's head and neck.

Additional Components

In one embodiment of the invention, the head positioning device 10 comprises a base portion 32. The elevating mechanism 16 is preferably attached adjacent the base portion 32 such that the elevating mechanism may adjust to support a patient's head in varying heights and angles, but is also structurally stable enough to prevent the head support 12 from shifting or moving out of position. Thus, the base portion 32 is preferably dimensioned to provide stability while the patient's head 14 is supported and properly positioned by the head positioning device 10. In the illustrated embodiment, the size and configuration of the base member 24 facilitates portability of the head positioning device. Thus, in various embodiments, the base portion 32 may be manufactured of a lightweight but durable material.

In addition, in various embodiments, the base portion 32 is typically at least as wide as the second support member 24. In certain embodiments of the invention, a table (e.g., an operating table) may be used as the base portion 32.

II. Operation of the Head Positioning Device

As noted above, in one embodiment of the invention, the head positioning device 10 is preferably configured for positioning a patient's head for endotracheal intubation, laryngoscopy, tracheoscopy, or a similar procedure. In addition, it should be understood that the head positioning device 10 may be used to facilitate other procedures in which, for example, a secure and stationary position of the patient's head is desired. Such procedures include, for example, various dental or eye procedures. In a particular embodiment, the head positioning device 10 is portable and may be easily disassembled and reassembled so that the device may be used in a variety of locations and situations.

To use a head positioning device 10 according to a particular embodiment of the invention, the patient's head 14 is first positioned adjacent the head support 12. More particularly, the posterior of the patient's head 14 is placed adjacent the concave curvature of the head support 12. The head restraint 20 is then positioned about the patient's head 14 to securely fasten the patient's head 14 adjacent the head support 12. Typically, the head restraint 20 is positioned so that it extends substantially circumferentially about the patient's forehead and the hook member 30 is positioned to hookedly engage the glabella of the patient's head 14. Once the hook member 30 is properly in position, the head restraint 20 may be secured and tightened (e.g., by locking the head restraint 20 in place adjacent the head support 12 in any appropriate manner). In various embodiments, once the patient's head 14 is secured by the head restraint 20 and hook member 30, rotation of the head support 12 causes a corresponding rotation of the patient's head 14.

In certain situations, the head positioning device's elevating mechanism 16 may need to be adjusted to accommodate a particular patient. This may be accomplished, for example, by manually moving the elevating mechanism 16 (e.g., by manually moving the head support 12, the elevating mechanism 16, and/or the patient's head 14). The elevating mechanism 16 is then adjusted until a desired amount of head elevation is achieved. In an additional embodiment, the elevating mechanism 16 is configured to be adjusted automatically, or to be adjusted both manually and automatically. For example, one or more pistons (e.g., pneumatic or hydraulic pistons) may be employed to raise and/or lower the head support 12 under the control of an appropriate control system. In various embodiments, the elevating mechanism 16 may be adjusted at any time and even prior to positioning the patient's head 14 within the head support 12.

As noted above, in one embodiment of the invention, once the patient's head 14 is secured adjacent the head support 12, the patient's head may be pivoted about a virtual axis of rotation projecting through (or approximately through) the mastoid region of the patient's head 14. In various embodiments, the patient's head 14 is rotated by pivoting the head support 12 about the head positioning device's sliding joint 18 to achieve a desired degree of neck extension and head dorsiflexion.

Typically, the patient's head 14 will initially be positioned first in a non-extended position (See FIG. 1) and will then be rotated about the virtual axis of rotation A to a "sniffing position," such as that depicted in FIG. 4. In various embodiments, the head positioning device 10 is then locked so that the head restraint 20 and/or hook member 30 maintain the patient's head 14 in dorsiflexion and the patient's neck in extension. The patient may then, for example, be intubated while in this position.

In various embodiments, a practitioner may pivot the patient's head 14 manually by moving the head support 12 and/or the patient's head 14. However, as discussed above with respect to the elevating mechanism 16, it should be understood that, in various embodiments, the head support 12 may also be pivoted about the sliding joint 18 automatically, or both manually and automatically. Thus, the head support 12 may be connected adjacent the sliding joint base member 26 with an automated track or bearing mechanism to automatically adjust the amount of head dorsiflexion and neck extension.

In various embodiments, the position of the patient's head 14 may be adjusted while the patient's head 14 is supported by the head support 12. In addition, in certain embodiments, the head support 12 may be pivoted about the sliding joint 18 at any time. For example, in such embodiments, the patient's head 14 may be rotated before (or as) the elevating mechanism 16 is adjusted. Furthermore, in various embodiments, the head positioning device 10 may be entirely pre-positioned for a particular patient such that adjustments are not be required after the patient's head 14 is secured by the head positioning device 10.

In one embodiment of the invention, the patient's head 14 may be removed from the head positioning device 10 by manually supporting the patient's head 14 and then loosening the head positioning device's head restraint 20 (by, for example, unlocking the head restraint 20 and then pulling it away from the rest of the head positioning device 10). Alternatively, the patient's head 14 may be lowered by the elevating mechanism 16 prior to removing the patient's head 14 from the head positioning device 10, and/or the patient's head 14 may be rotated about the virtual axis of rotation to reduce the amount of neck extension and head dorsiflexion prior to removing the patient's head 14 from the head positioning device 10.

III. Conclusion

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

I claim:

1. A head positioning device comprising:
a head support that is configured for supporting a patient's head, said head support being configured for engaging a rear portion of said patient's head; and
a head restraint disposed adjacent said head support, said head restraint comprising a hook member that is configured for: (A) hookedly engaging a curved portion of said patient's face; and (B) exerting a force adjacent said curved portion of said patient's face, said force being sufficient to rotate said patient's head so that said patient's forehead moves away from said patient's chest.

2. The head positioning device of claim 1, wherein:
said head positioning device further comprises a sliding joint that is disposed adjacent said head support and adapted to allow said head support to move along a substantially arcuate path while said head support is supporting said patient's head; and
said hook member is configured for exerting said force adjacent said curved portion of said patient's face in response to said head support being moved along said substantially arcuate path.

3. The head positioning device of claim 2, wherein said arcuate path lies substantially along the circumference of a circle having its center along an axis that extends through a mastoid region of said patient's head.

4. The head positioning device of claim 3, wherein said circle is substantially parallel to said axis.

5. The head positioning device of claim 2, wherein said force is sufficient to maintain said patient's head in a sniffing position while said patient is being intubated.

6. The head positioning device of claim 2, wherein said hook member is configured for hookedly engaging said patient's glabella.

7. The head positioning device of claim 6, wherein said hook member is configured for exerting said force adjacent said patient's glabella.

8. The head positioning device of claim 7, wherein said force is sufficient to maintain said patient's head in a sniffing position while said patient is being intubated.

9. The head positioning device of claim 2, wherein said head restraint further comprises a head restraining portion that is configured to extend around at least a portion of said patient's forehead while said head support is being moved along said substantially arcuate path.

10. The head positioning device of claim 9, wherein said head restraint further comprises a padding portion that is configured for being disposed between said patient's forehead and said head restraining portion while said head support is being moved along said substantially arcuate path.

11. The head positioning device of claim 9, wherein said head restraining portion is substantially rigid.

12. The head positioning device of claim 1, wherein said force is sufficient to rotate said patient's head about a virtual axis of rotation between a non-extended position and a "sniffing" position.

13. The head positioning device of claim 12, wherein said virtual axis of rotation extends through a mastoid region of said patient's head.

14. The head positioning device of claim 12, wherein said virtual axis of rotation extends proximate a mastoid region of said patient's head.

15. A head positioning device comprising:
a head support that is configured for supporting a patient's head, said head support being configured for engaging a rear portion of said patient's head; and
a head restraint disposed adjacent said head support, said head restraint being configured for: (A) engaging a portion of said patient's face; and (B) exerting a force adjacent said portion of said patient's face, said force being sufficient to rotate said patient's head into a sniffing position while said head support is supporting said patient's head.

16. The head positioning device of claim 15, wherein said head restraint comprises a head restraining portion that is configured: (A) to extend around at least a portion of said patient's forehead while said head positioning device is being used to move said patient's head into said sniffing position; and (B) to maintain said patient's head in a substantially fixed orientation relative to said head support while said head positioning device is being used to move said patient's head into said sniffing position.

17. The head positioning device of claim 16, wherein said head restraining portion is substantially rigid.

18. The head positioning device of claim 16, wherein said head restraining portion is configured to extend substantially entirely around said patient's forehead while said head positioning device is being used to move said patient's head into said sniffing position.

19. The head positioning device of claim 18, wherein said head restraining portion is configured to maintain said patient's head in said sniffing position while said patient is being intubated.

20. The head positioning device of claim 19, wherein said head restraint comprises a hook member that is configured: (A) to hookedly engage a portion of said patient's face; and (B) to exert a force on said portion of said patient's face, said force being sufficient to facilitate moving said patient's head into said sniffing position.

21. The head positioning device of claim 20, wherein said head positioning device further comprises:
   a base member that is spaced apart from said head support; and
   an elevating mechanism that is adapted to move said head support between: (A) a first position in which said head support is spaced apart from said base member by a first distance, and (B) a second position in which said head support is spaced apart from said base member by a second distance.

22. The head positioning device of claim 15, wherein:
   said head positioning device further comprises a sliding joint that is disposed adjacent said head support and adapted to allow said head support to move along a substantially arcuate path while said head support is supporting said patient's head.

23. The head positioning device of claim 22, wherein said arcuate path substantially lies along the circumference of a circle having its center along an axis that extends through a mastoid region of said patient's head.

24. The head positioning device of claim 23, wherein said circle is substantially perpendicular to said axis.

25. The head positioning device of claim 15, wherein said force is sufficient to rotate said patient's head about a virtual axis of rotation between a non-extended position and a "sniffing" position.

26. The head positioning device of claim 25, wherein said virtual axis of rotation extends through a mastoid region of said patient's head.

27. The head positioning device of claim 25, wherein said virtual axis of rotation extends proximate a mastoid region of said patient's head.

* * * * *